US006402782B1

(12) United States Patent
Sibbald et al.

(10) Patent No.: US 6,402,782 B1
(45) Date of Patent: Jun. 11, 2002

(54) ARTIFICIAL EAR AND AUDITORY CANAL SYSTEM AND MEANS OF MANUFACTURING THE SAME

(75) Inventors: Alastair Sibbald, Berkshire; George Derek Warner, deceased, late of Middlesex, both of (GB), by Johanna Warner, legal representative

(73) Assignee: Central Research Laboratories, Limited, Hayes (GB)

( * ) Notice: Subject to any disclaimer, the term of this patent is extended or adjusted under 35 U.S.C. 154(b) by 0 days.

(21) Appl. No.: 09/403,523

(22) PCT Filed: May 15, 1998

(86) PCT No.: PCT/GB98/01407

§ 371 (c)(1), (2), (4) Date: Jan. 13, 2000

(87) PCT Pub. No.: WO98/52382

PCT Pub. Date: Nov. 19, 1998

(30) Foreign Application Priority Data

May 15, 1997 (GB) ............................................ 9709848

(51) Int. Cl.[7] .................................................. A61F 2/18

(52) U.S. Cl. ...................................................... 623/10

(58) Field of Search ............................ 623/10, 11, 909, 623/912, 915, 919, 920, 923, 924, 926

(56) References Cited

U.S. PATENT DOCUMENTS 5,033,086 A * 7/1991 Fidi ........................... 381/310
5,553,152 A * 9/1996 Newton ...................... 381/328
5,597,380 A * 1/1997 McDermott et al. ........ 607/137

* cited by examiner

*Primary Examiner*—Corrine McDermott
*Assistant Examiner*—Hieu Phan
(74) *Attorney, Agent, or Firm*—William H. Bollman

(57) ABSTRACT

A laminated artificial pinna having a concha, fossa and auditory canal. The auditory canal is constructed and arranged relative to the concha so that the distance from the center of the entrance of the auditory canal to the rear wall of the concha lies within the range of 15 mm to 20 mm, the distance from the center of the entrance of the auditory canal to the concha floor lies within the range of 9 mm to 15 mm, and the alignment of the turning point with the center of the entrance of the auditory canal is substantially horizontal.

23 Claims, 7 Drawing Sheets

ARTIFICIAL EAR AND AUDITORY CANAL SYSTEM AND MEANS OF MANUFACTURING THE SAME

The present invention relates to a novel artificial ear and auditory canal system, and a means of manufacture of the same.

The invention has particular application in the field of binaural, three-dimensional sound recording and associated techniques, and also in the fields of noise measurement and hearing prostheses development.

Artificial head recording systems are now well known (see for example U.S. Pat. No. 1,855,149) A typical artificial head system comprises a pair of microphones mounted on to the sides of an artificial head assembly where the auditory canal would be, inset into a pair of artificial pinnae (the visible ear flaps). A recording made with an artificial head incorporates many of the 3D sound “cues” which our brains use to interpret the positions of sound sources in 3D space, and so such recordings provide quite dramatic 3D effects when auditioned over headphones. More recently, it has become possible to make acoustic measurements on artificial heads (the measurement of Head-Response Transfer Functions—HRTFs), and synthesise the effects of the head and ears electronically, using digital signal-processing. However, although these effects are initially perceived to be quite dramatic, especially when heard for the first time, several major deficiencies in present-day artificial heads become apparent when they are tested more rigorously.

The two prime deficiencies are (a) poor “height” effects, and (b) poor front-back discrimination. For example, in respect of (a), this means that when a recording is made of a sound-source moving over the top of the head (from, say, a position close to the left ear, over the head to a position close to the right ear), then the sound-source appears to move directly through the head, rather than over the top. In respect of (b), if a recording were made of a sound-source moving around the artificial head in the horizontal plane in a circle of constant distance (say 1 meter), then the recorded source would appear to move back and forth in arcs from the left ear to the right, always in front of the listener and never behind. These spatial inaccuracies are often overlooked or ignored for recording purposes, where most real-life sound-sources are in front of the artificial-head/listener, and not in these more extreme positions. Nevertheless, the poor spatial accuracy of presently available artificial heads prevents the synthesis of an adequate 360° sound-field, such as is required for computer games applications, immersive virtual reality, simulators and the like.

Many researchers have been puzzled over why their artificial head systems are inadequate in the above respects. Some have turned to making measurement on real head-ear systems, by embedding miniature microphones in the pinnae or auditory canals of experimental volunteers. Others have resorted to building their own artificial head systems, attempting to improve on the products of commercial manufacturers, and, in some cases, have taken molding from the ears of volunteers for replicating and using. In one extreme example, U.S. Pat. No. 4,680,856 (Zuccarelli) attempted to replicate or simulate the entire anatomy of the skull, including the bones, double-twisted oval auditory canals, Eustachian tubes, teeth and skin, in order to copy reality as closely as possible. Zuccarelli even stated that a wig was necessary in order to provide good front-back discrimination! Clearly, this latter approach is totally unsuitable for a manufactured product in terms of expense and operational factors (weight, bulk and appearance). In addition, this approach does not allow for the creation of a system with adequate Left-Right matching, because very small L-R differences, introduced during manufacture, in the size, shape or position of any of the acoustic cavities in the structure create significant differences in the overall properties and HRTFs.

The first demonstration of a stereophonic effect is believed to have taken place in Paris in the 1890s, when multiple microphones situated in an array across the front of a stage were each connected to individual ear pieces in an adjacent room, and listeners found that the use of adjacent pairs of ear pieces (and hence microphones) provided very realistic sound reproduction with spatial properties. The first explicit report of a dummy-head type of sound reproduction method appears in U.S. Pat. No. 1,855,149, dated 1927 in which the purpose was to record sounds in such a way that the natural, head-related time-of-arrival and amplitude differences between L and R signals were convolved acoustically on to the sounds, and then replay was achieved using either earphone reproducers or equidistant loudspeakers, placed directly to the left and right of the listener, such that “the virtual sound origins were secured”. British Patent No.394325 (Blumlein) filed in 1931 relates to conventional, present-day stereo in which the use of two or more microphones and appropriate elements in the transmission circuit were used to provide directional-dependent loudness of the loudspeakers, together with means to cut discs and thus record the signals. Stereo sound recording and reproduction was not commercially exploited widely until the 1950s.

At the present time, conventional stereo is largely Blumlein’s amplitude-based stereo, in which a number of individual, monophonic recordings are effectively “placed” spatially in the sound-stage between the listener’s loudspeakers by virtue of their L-R loudness differences. This is achieved by “pan-potting”. It is possible to add artificial reverberation and other effects to enhance the spatial aspects (room acoustics, and distance) of these recordings.

When live recordings are being made, it is common to use stereo microphone pairs, placed so as to be either (a) coincident, or (b) spaced-apart by about one head-width, or thereabouts. This latter goes part-way to the reproduction of a natural acoustic image of a performance, but there have been several periods since the 1950s when the use of the dummy-head recording method for producing binaural signals has been experimented with for improving the quality of the stereo image.

Historically, the term “stereophonic” was coined in the 1950s to apply to sound reproduction over two or more transmission channels. In the 1970s, there was a resurgence of interest in recording using dummy-head microphone techniques, and the expression “binaural” was coined exclusively for recordings made by such means. More recently, the term “binaural” has also been used for electronic equivalents, where the acoustic processing effects of the human head and external ear are synthesised.

Dummy-head (binaural) recording systems comprise an artificial, life-size head and sometimes torso, in which a pair of high-quality microphones are mounted in the ear auditory canal positions. The external ear parts are reproduced according to mean human dimensions, and manufactured from silicon rubber or similar material, such that the sounds which the microphones record have been modified acoustically by the dummy head and ears so as to possess all of the natural sound localisation cues used by the brain.

Following on from the development of somewhat crude and simple artificial heads for binaural sound recording in the 1930s and 1940s, acousticians became aware that these head structures were ideal platforms for testing and evaluating hearing aids and other devices, such as hearing defenders (ear-plugs). Consequently, a more academic interest was taken in the development of artificial heads, with more care taken in their construction and engineering. For example, the papers by Torick (An electronic dummy for accoustical testing E. L. Torick et al., J. Audio Eng. Soc., October 1988, 16, (4), pp. 397–402) and Burkhardt and Sachs (Anthropometric manikin for acoustic research M D Burkhardt and R M Sachs, J. Acoust. Soc. Am., July 1975, 58, (1), pp. 214–222) are two excellent papers to study for more information about artificial heads. It soon became clear that, although the simple, earliest head structures were adequate for binaural recording, they were poor representations of the human anatomy. The prime reason is that the early recording heads were fitted with microphones in which the microphone grid was mounted flush with the concha valley floor (see FIG. 1 for ear terminology), and not at the end of a simulated auditory canal. Although this is not a problem for sound recording situations, it is clearly not suitable for the development of in-ear hearing aids, where the actual presence and acoustic impedance of the auditory canal itself becomes an important feature. In order to remedy this omission, Professor Zwislocky, of Syracuse University, devised an acoustic coupler to mimic the properties of the auditory canal. This was described in several internal University reports, and was later developed commercially for use in the KEMAR manikin by Knowles Electronics, (U.S. Pat. No. 5,033,086) who improved on the original structure from the manufacturing point of view. The Zwislocki coupler is a stainless-steel, cube-like structure, measuring 21.5×21.5×15 mm, featuring an entrance port on one face, for coupling to an artificial ear, and a 12 mm microphone port on the opposite face. On each of the remaining four faces, there is coupled a small, tuned acoustic circuit side-branch. Each side-branch has a particular specific inertance, resistance and compliance, such that the overall impedance versus frequency characteristics of the coupler match those of the average adult human, with great accuracy, up to about 8 kHz. Beyond this, it was supposed that the reflective surface of the microphone diaphragm becomes too dissimilar to that of the eardrum to accommodate.

In terms of acoustic research, this form of ear coupler, together with similar products made by different manufacturers, became adopted for applications where very high accuracy of auditory canal simulation was necessary. However, for audio recording, the auditory canal presents a severe practical problem, in that the primary quarter-wave resonance of the auditory canal simulator creates a very substantial boost—often 10 to 15 dB—at around 3.9 kHz, and this adds to the equally substantial resonance of the concha cavity at about 2.8 kHz. The consequence is that there is a major 25 to 30 dB resonant peak at around 3 kHz which must be compensated, or else the recordings are tonally very incorrect. Correction of such a gross anomaly is possible. It is difficult to achieve using analogue methods, but is feasible using digital filtering. However, even when this is accomplished, there is still a signal-to-noise penalty to pay, because the resonant boost has effectively pushed the non-resonant regions of the response by 30 dB towards the noise floor of the system. Additionally, the use of 12 mm microphones mandates the use of non-studio type microphones, with poorer noise performance. For these reasons, non-auditory canal based head systems are still preferred for studio recordings, where the best possible signal-to-noise ratios are demanded. Research by Shaw and Teranshi (Paper entitled "Sound Pressure Generated In An External-Ear Replica and Real Human Ears By a Nearby Point Source" by E A G Shaw and R Teranshi, J. Acoust. Soc. Am., 1968, 44, (1), pp. 240–249), indicated that the sound pressure levels (SPLs) scale linearly from the auditory-canal entrance to the eardrum, and so the use of artificial heads without auditory canal simulators has been claimed to be valid. However, this result must be viewed with great caution, because of their experimental methods, since introducing even the smallest measurement transducer into either the pinna or auditory canal affects the overall acoustic properties of the ear in a substantial way.

There are several types of artificial heads available commercially at the present time. The following four, described below, are the most widely used types, although we have heard of several other Japanese and American types from smaller manufacturers. The main features are noted below.

A known artificial head (B&K type 4100) manufactured by Bruel & Kjaer features an artificial head mounted on to a torso simulator, fitted with a sound dampening fabric, which fits over the neck of the manikin. The head is in the form of a hollow "shell", with the microphones mounted directly on to metal plates on the sides of the shell assembly. The neck can be adjusted so that it tilts forwards, to an angle of 17 degrees. The pinna simulators are silicone rubber types, dimensioned to EC 959 and CCITT P.58, except for the ear-canal extensions, with B&K 4165 microphones mounted in the concha cavity. Overall weight is 7.9 kg.

Another known artificial head, the Ku 100 is the successor of the well-known Ku80 and Ku81 series heads which have been manufactured by Georg Neumann GmbH and used since the late 1970s. The Ku80 was improved and renamed Ku81 in 1981, and there have been several variants using "i" affixes claiming improved loudspeaker compatibility (this might relate to changes in the EQ filters). The head is a solid, rubber-filled element, which can be spilt front-back to access the microphones and battery compartment. The head is fitted with artificial auditory canal-type microphone couplers, and uses Neumann 21 mm, KM100 series miniature condenser microphones, with in-built FET preamps. The head is fitted with electronic equalisation, probably analogue filters, which is battery driven and is located in the head itself The head is suitable for hanging or tripod mounting, and does not have shoulders. It weighs 2.7 kg, and is matt black.

Another well known artificial head, the Aachen (Head Acoustics) system 15 manufactured by Head Acoustics GmbH (see U.S. Pat. No. 4,631,962) is different to other artificial heads in that it is based on a much-simplified structure, which the inventor claims is representative of the important features of human hearing. The ear shapes and head dimensions conform to a set of equations which simplify the construction of the head. It was developed initially for noise measurement in the automotive industry. The head is suitable for tripod mounting, and has shoulders which can be attached, if required. It weighs 7 kg, and is matt black. An equalisation unit is usually supplied with the head.

A further well known artificial head system is the KEMAR manufactured by Knowles Electronics Inc., [Knowles Electronics Manikin for Acoustic Research.] This manikin system was developed in the 1970s, and has been widely used for the research and development of hearing aids. The system is available in modular form, including an optional torso. The head is hollow, splitting around the upper skull periphery, and the inner surfaces have been coated with lead-filled epoxy in order to dampen any resonances reduce the transmission of sound through the shell itself. 12 mm B&K microphones are fitted to the shell using Zwislocki couplers, and the coupler inlets are connected directly to openings in the silicon rubber pinnae. The pinna rubber is a mixture of two different types in order to simulate as closely as possible the mechanical properties of the human ear. Several different neck units are available, with differing heights. Various ear types are available, too, for different applications.

None of the aforementioned commercial heads give adequate "height" cues, and they also have poor front-back discrimination, due to the relative inefficiency of the artificial ears that have been used in the past.

Some researchers have replicated ears by taking molding from either real ears or sculpted copies of real ears. However, this is not satisfactory for the following reasons.

(a) The Left to Right matching is very poor, and cannot be corrected or adjusted.

(b) Molding errors are present, which introduce shrinkage and distortion.

(c) There is no control over the dimensions, and so particular values cannot be specified.

(d) The mating arrangements between the ear unit and the auditory canal or microphone mount are not well-defined. We have discovered that the mating arrangements and the auditory canal or microphone mount are a very critical feature.

It is very difficult to mold artificial ears accurately because of shrinkage of the molded parts. Furthermore it is difficult to use a machine to manufacture a three-dimensional structure such as an ear because of the deep undercuts. It could be achieved, perhaps, by making several 3D "blocks", and then assembling them, but this would be difficult to arrange and would require interlocking alignment lugs in three-dimensional format.

There are many claims in the literature which we have discovered to be incorrect. For example, it is common to claim that the type of materials which are used for the pinnae, skin and other features are important and that artificial ears must be made of materials, such as latex or rubber that have a similar texture or feel as human ears. We have found by experiment and measurement that the material from which the pinna is made is relatively unimportant acoustically, and that the simulation of skin is unnecessary. Duda R O 'Modeling Head Related Transfer Functions' Proceedings Of The Asilomar Conference, Pacific Grove, Nov., 1–3. 1993, Vol2, Nov. 1, 1993, Institute Of Electrical And Electronics Engineers, pages 996–1000 XP000438445, discloses that Head Related Transfer Functions (HRTFs) characterise the transformation of a sound source to the sounds reaching the eardrums and are central to binaural hearing. Because they are the result of wave propagation and diffraction, they can only be approximated by finitely parameterised filters. The functional dependence of the HRTF on aximuth and elevation is described in this paper, and various artificial head models are described. Many of the described models including that of U.S. Pat. No. 4,631,962 (Genuit), do not replicate the geometry of the human pinna with sufficient precision to produce precise HRTFS. Therefore it is difficult even with with finitely parameterised filters to produce an acceptable HRTF.

The prior art suggests that hard materials are unsuitable for the fabrication of artificial ears for acoustic measurements because their properties are very dissimilar to those of skin. However, we have discovered by comparison of HRTF measurements that, on the contrary, the choice of materials is not significant. Indeed we prefer to use hard materials because of their constancy of physical dimensions (rubber ears can sag and become twisted, thus distorting the shapes and dimensions of their acoustic cavities, and hence significantly changing the associated HRTFs).

An object of the present invention is to provide an accurately dimensioned artificial pinna and auditory canal which provides improved cues as to the height of sources of sound and improved front-back discrimination, utilising materials which conventionally would not normally be considered appropriate for artificial pinnae and which can be manufactured in a controlled, reproducible way, preferably by computer control.

There are known methods of constructing three dimensional articles by building up the article from laminations. Examples of such are to be found in International Patent Applications WO91/12957 and WO87/07538, European Patent Applications 0633129 A1, and 0667227A2, U.S. Pat. No. 5,031,483 and British Patent Application 2,297,516A.

In particular U.S. Pat. No. 5031.483 discloses a technique for making molds by stacking a plurality of sheets, each of which has a shape machined out it. The sheets are stacked to form the finished article.

To an expert in designing artificial pinnae it would not normally be considered appropriate, or desirable, to reconstruct a replica human pinna using a laminated construction because of the creation of multifaceted or stepped edges. One's initial impression is that such steps or inconsistencies formed at each interface of the laminae would detract from the overall acoustic performance of the artificial ear. On the contrary, we have found that it is possible to 'adjust' the profiles of the laminae (without necessarily eliminating stepped changes from one laminae to the next) and still optimise the overall acoustic performance of the artificial ear.

A further object of the present invention is to provide a means of providing adequate directional information suitable for recording and for providing appropriate data for 3D-sound synthesis. According to one aspect of the present invention there is provided a method of manufacturing a laminated artificial pinna comprising the steps of:

(a) forming a three dimensional model of a human pinna in a first material, (b) encapsulating said model in a molding material, (c) machining away the encapsulated model to reveal a cross sectional shape of the model.

(d) making an image of the cross sectional shape revealed by step (c), (e) repeating step (c) incrementally to reveal cross sectional shapes of the model in spaced parallel planes and repeating step (d), (f) providing a plurality of blank self supporting sheets of material of a thickness corresponding to the distance between said spaced parallel planes, and using the image produced by step (d) to produce a replica of the cross sectional shape of the model pinna supported from each sheet of material by bridging supports.

(g) repeating step (f) for each cross-sectional shape revealed by step (c), and (h) assembling and gluing together a stack of said sheets to define a laminated replica of said model.

Preferably step (d) comprises the step of deriving from said image, data for controlling the direction of movement of a cutting tool, and step (f) comprises machining each sheet of material with a cutting tool programmed to move under control of the data derived by step (d).

Preferably step (f) comprises the step of using the image produced by step (d) to produce a mask corresponding to said image, and step (f) comprises the step of removing unmasked material.

The sheets of material may be photosensitive and the unmasked material is removed by exposing the masked sheets to light and a developer.

Preferably an artificial auditory canal is attached to the laminated replica of said model.

The model may be made of a rigid plastics material, and the molding material is a rigid plastics material of a different color to that of the model. The image may be derived by electronically scanning a cross section of the encapsulated model, or derived by photocopying a cross section of the encapsulated model.

Preferably the image is converted to a digitised electronic image. The electronic image may be used to derive a binary computer control code for controlling the direction of movement of a C.N.C. machine cutting tool.

According to a further aspect of the invention there is provided a laminated artificial pinna, constructed in accordance with the latter mentioned method.

Preferably the artificial pinna has a laminated artificial pinna according to claim 12 characterised in that the artificial pinna how a concha, fossa and auditory canal and the auditory canal is constructed and arranged relative to the concha, so that the distance ((A) of FIG. 7) from the center of the entrance of the auditory canal 23 to the rear wall of the concha 12 lies within the range of 15 mm to 20 mm, the distance ((B) of FIG. 8) from the center of the entrance of the auditory canal to the concha floor lies within the range of 9 mm to 15 mm, and the alignment of the turning point ((C) of FIG. 9) with the center of the entrance of the auditory canal is substantially horizontal.

In a preferred embodiment an artificial pinna according to claim 14 herein the bore 27 of our auditory canal 23 comprises a right circular cylindrical bore 27 having a radious and a length ((a) of FIG. 13), measured from an open end of the bore 27 along a central axis of the bore 27 to the plane 29 of the pressure sensitive face 34 of the microphone 33 which is such as to define a resonant cavity having a fundamental resonance of 3.9 KHz.

The bore may be dimensioned so that the dimension of the sum of the length ((a) of FIG. 13) and the radius of the bore equals 22 mm. For example, the diameter of the bore is 7 mm, the angle of the plane of the pressure sensitive face of the microphone is 45° to the longditudial axis of the bore, and the length of the bore is 18.5 mm.

Preferably the distance from the central axis of the bore of the auditory canal to the rear wall of the concha is 16.6 mm (average), and the distance from the canal axis to the floor of the concha is 11.3 mm (average).

According to a further aspect of the present invention there is provided a method of recording sound using artificial ears having pinna manufactured according to the method claimed of claim 1, wherein sound waves received by the artificial ears are converted to an electrical signal and are processed by a signal processor having signal filters, the head related transfer functions of which are derived from signal processing algorithms based on measurements corresponding to the measurements of the artificial pinna and auditory canals of the artificial ears which are used to make the recording.

The present invention will now be described by way of an example and with reference to the accompanying drawings in which:FIG.

Figure 1:
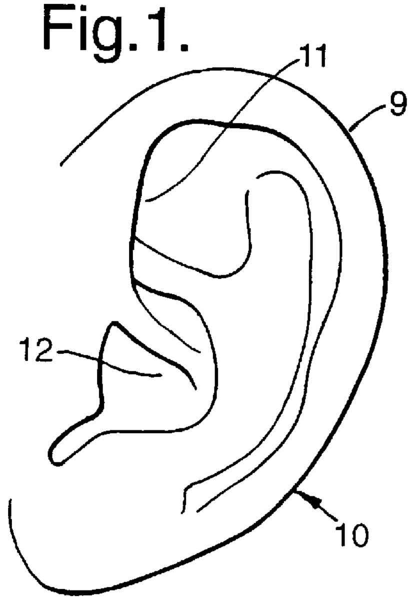
FIG. 1 illustrates schematically the main parts of a human pinna.

Referring to FIG. 1, the main parts of a human pinna 10 (the outer ear flap) comprise a fleshy peripheral fold of skin called the scapha 9, a resonant cavity called the fossa 11 at an uppermost region of the pinna, and the Concha 12 which is a resonant chamber which leads to the auditory canal (not shown) where the tympanic membrane (ear drum) is located. The fossa 11 is particularly responsive to high frequency sounds of the order of 15 kHz and it is that part of the Pinna which contributes to the formation of the cues that enables the brain of the listener to discriminate between sounds emanating from the front or back of the head as well as the height of the source of sounds. Details of the auditory canal and the components of the inner ear are not shown in FIG. 1.

Figure 2:
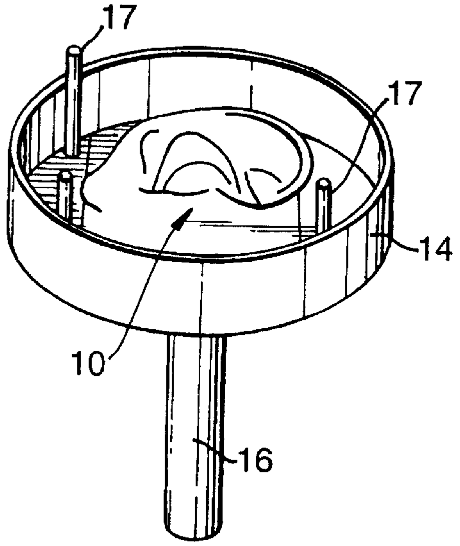
FIGS. 2 to 5 show various stages in the manufacture of an artificial pinna for use in an artificial ear constructed in accordance with the present invention.

Referring to FIG. 2, a pair of "reference" pinnae is created, typically in a hard plastic material such as polyurethane. This is done by sculpting an artificial pinna 10 by cutting and shaping the polyurethane and, by means of a series of re-iterative experiments, successively modifying the physical attributes of the sculpted pinna. Each sculpture is subjected to listening tests to ascertain the spatial properties and adjustments of shape and dimensions made. For example, one can change the depth of the fossa cavity 11 and, using microphones located where the ear drum would be, hear what effect this has on the spatial properties of the pair of pinnae When a satisfactory pinna shape is finally achieved—suitable for a wide range of listeners—then each pinna 10 is placed in a molding dish 14 as shown in FIG. 2 and encapsulated completely with a molding epoxy or resin 15, of a different color to that of the sculpted pinna. The molding dish 14 is fitted with a spindle 16 projecting from the lower face, such that it can be mounted in a lathe (not shown). Alternatively the mold dish 14 could be mounted for milling in a milling machine. In addition, the molding dish 14 has three narrow rods or tubes 17, extending in a direction normal to the base of the molding dish 14. These rods 17 are placed around the pinna 10 and provide a means for alignment and spatial reference measurements.

Figure 3:
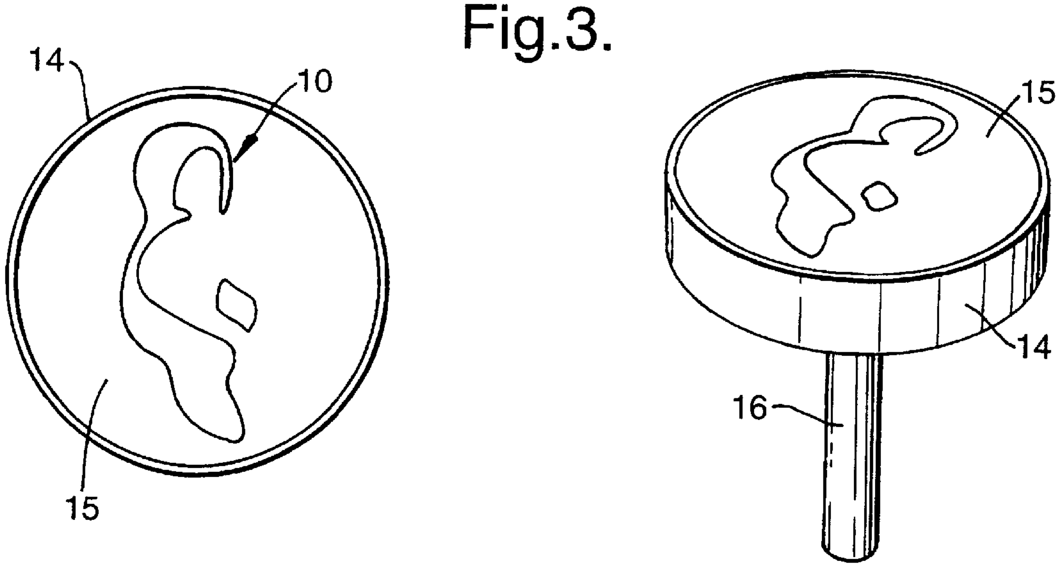

The molding dish 14 with the encapsulated pinna 10 is fitted into a lathe (or milling machine), and the molding is carefully skimmed down gradually from the outermost face until the first section of the pinna 10 (the tip of the scapha 9) is revealed. A further 1 mm section is removed by carefully advancing the cutting tool of the lathe a distance of 1 mm, and the resultant exposed section of the molding, including the reference rods 17 is imaged using a scanner or a photocopier. Another 1 mm section is then machined away, and then a further image of the newly exposed section is made using a scanner or photocopier. A typical cross section is shown in FIG. 3. This process is repeated until the base of the pinna 10 has been reached and the entire body of the encapsulated pinna 10 has been skimmed away. Typically, the whole process involves twenty-five cross sectional images taken in parallel planes spaced I mm apart.

The set of images of the cross sections of the pinna 10 are each individually digitised, using a computer tablet, and the digitised sections are edited to remove any errors and provide any required interpolation or smoothing between adjacent images. The digitised images are used to generate the co-ordinates to control the direction of movement of a cutting tool of a CNC milling machine as will be explained hereinafter.

Figure 4:
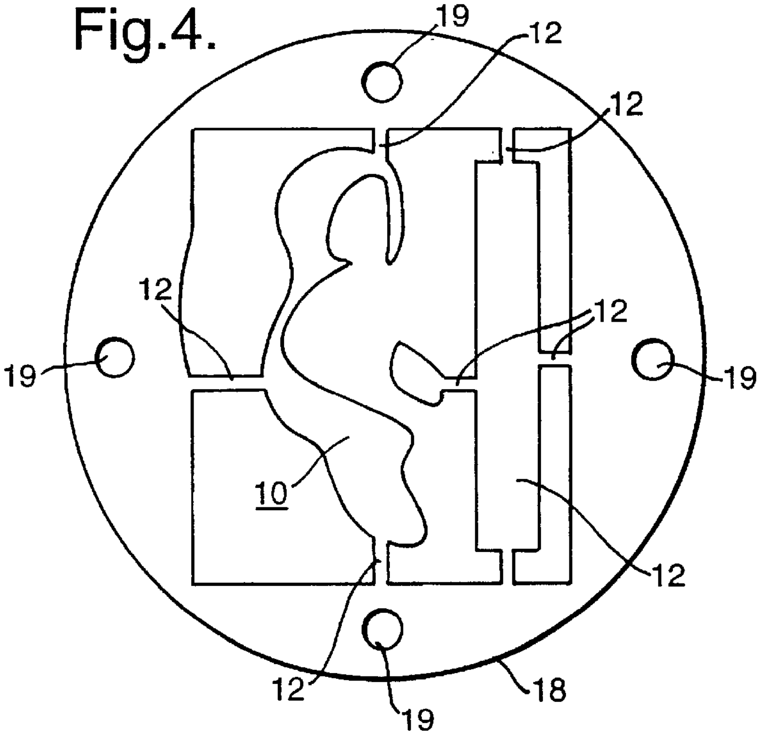

Next, referring to FIG. 4, support collars 18 are designed around each layer of the digitised ear, and connected to them by narrow, 2 mm thick webbing elements 12, in order to enable subsequent assembly. Jig assembly holes 19 are also added to each layer of the design. Next, each lamination element (FIG. 4) is cut from 1 mm thick, hard polystyrene sheet. Each lamination element, including the cross sectional shape of the pinna 10, is cut out under the control of the CNC commands derived from each of the digitised images. The cutting tool is programmed to cut out the shape of the pinna 10 but to leave bridging supports 12 extending between the pinna section and the periphery of the support collar 18.

In an alternative method of forming the laminations, instead of producing a digitalised image and cutting out the shapes using a C.N.C. machine the shapes could be produced by a photo-etching or chemical etching technique.

For example, the support collars 18 could be made from a photo-sensitive polymer such as a polyimide, known as Brewers T1059. The images taken of each cross sectional shape of the molded pinna 10 may be used to make a photo-resist mask which is applied to the surface of support collar 18. The unwanted material removed by exposing the masked support collars to ultra violet light and a developer, in the usual way.

It may also be possible to make the support collars 18 from a chemically etchable metal and to chemically etch suitably masked support collars.

Figure 5:
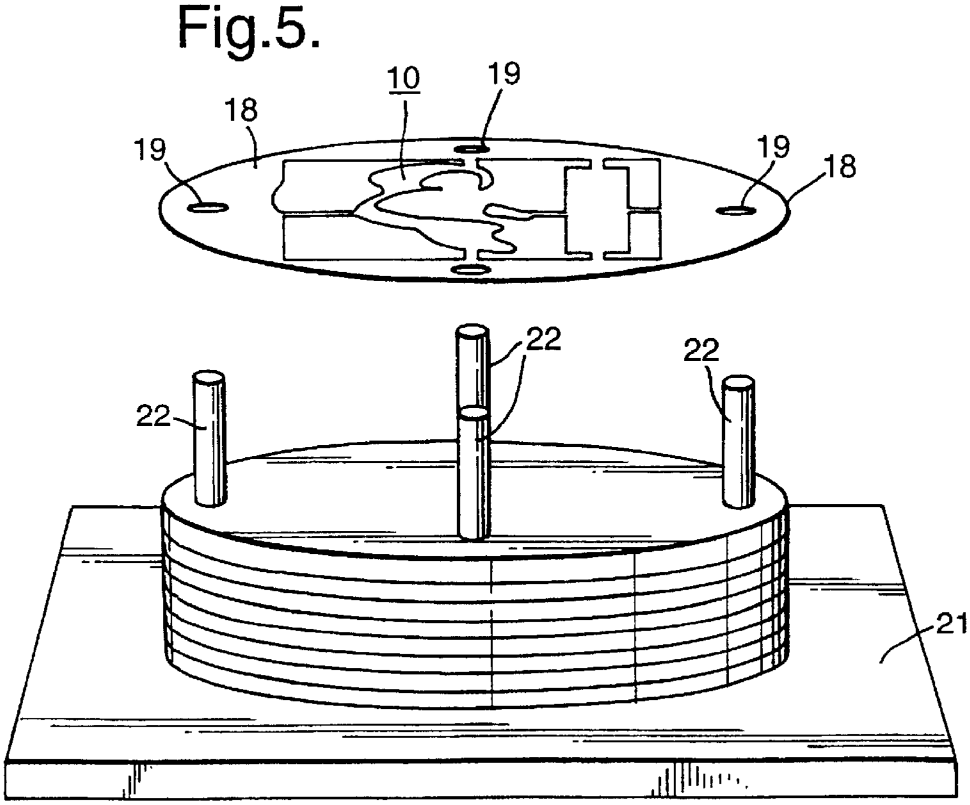

When all the lamination elements have been cut, they are stacked layer by layer, in a jig 21 as shown in FIG. 5, which has locating rods 22 equispaced around the jig 21. At this stage, the stack of laminates, resembles a quantised reproduction of the original, skimmed reference pinna 10. The first few layers, comprise a rectangular, mounting-base connected to the support collars 18 by bridging supports 12. The rectangular mounting base and bridging supports 12 of the first few layers 18 are glued together using an appropriate adhesive (such as a solvent glue, if polystyrene is used). As each successive lamination element is slotted on to the locating rods 22 of the assembly jig 21, only the pinna sectional shapes 10 are glued together, and the bridging supports 12 remain unglued, and are cut away after each individual layer is glued. Consequently, the upper layers, say layers 6 to 25, are all attached only to the previous layer, by the glued pinna sections 10, whereas layers 1 to 5 are also attached to the collar 18 by the bridging supports 20. In this way, the stack of glued discs 18 remain in register with the locating rods 22 of the jib 21 during assembly of the artificial pinna. When the glue is set, the completed pinna 10 is freed from the collars 18 by cutting the few remaining bridging supports 20 of the lower layers.

Figure 6:
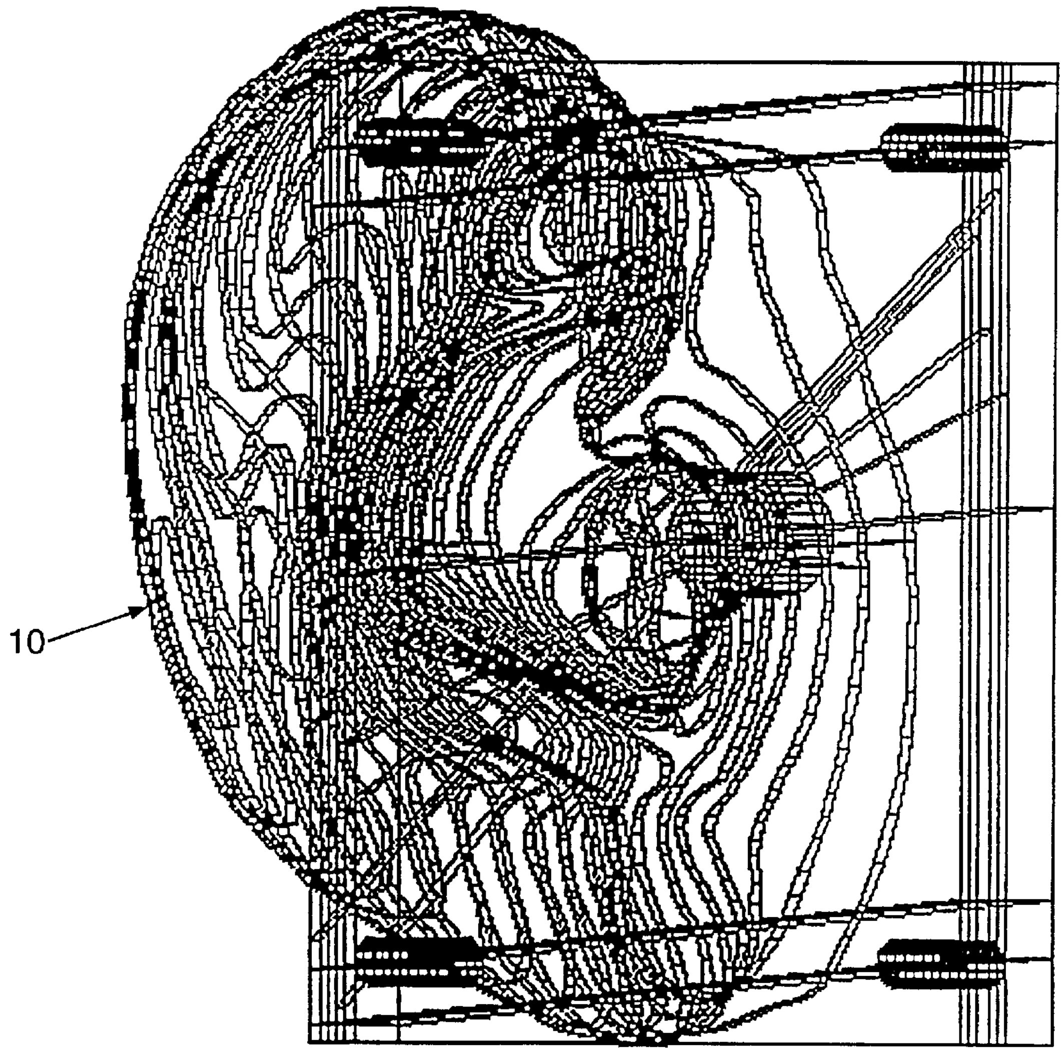
FIG. 6 shows a computer generated "wire frame" drawing of an artificial ear constructed in accordance with the present invention.

A computer generated "wireframe" diagram of a completed pinna 10 is shown in FIG. 6.

When manufacturing the artificial pinna 10 as described above it is vitally important to ensure that several critical dimensions and physical placements are correct. The features which we have discovered to be critical, and which are not present in the prior art are as follows.

Figure 7:
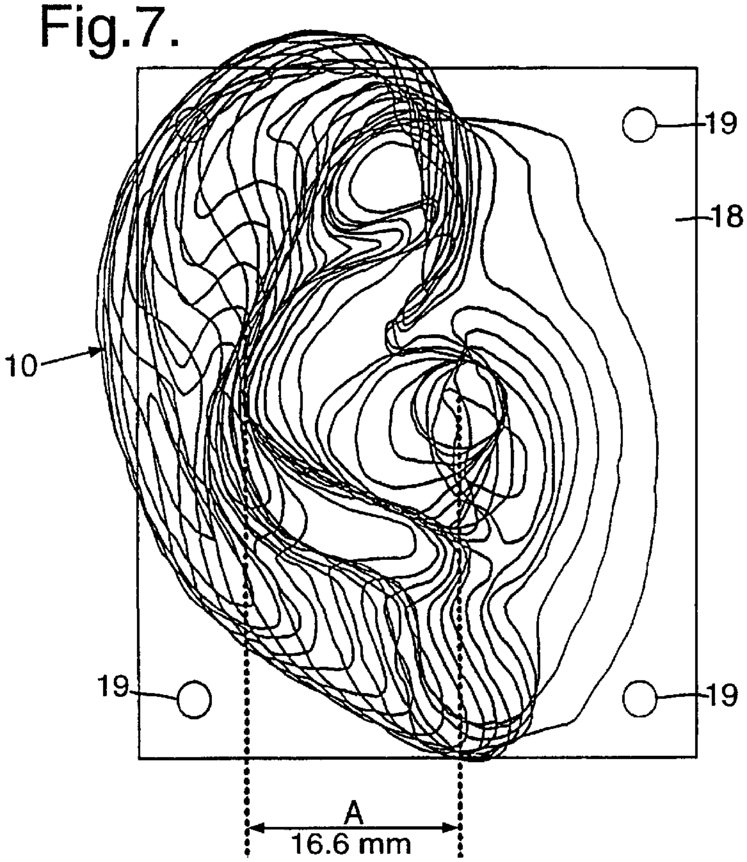
FIGS. 7 to 9 are a computer generated diagrams of various cross sectional topographies of an artificial ear constructed in accordance with the present invention showing critical features of the design of the artificial ear.

(a) The Fossa 11 must be adequately deep. This is difficult to describe or quantify, other than we know that certain prior known artificial pinnae are inadequate, and that a pinna constructed by the present invention was adequate with a volume of between 0.2 cc and 0.7 cc and preferably 0.5 cc (b) The distance from the center of the auditory canal entrance to concha rear wall (refer FIG. 7) is critical. We have found that a distance between 16 mm and 20 mm is a suitable and an average value of 16.6 mm is preferred (although our prototypes had a slightly larger distance (18.5 mm) and still function quite well).

Figure 8:
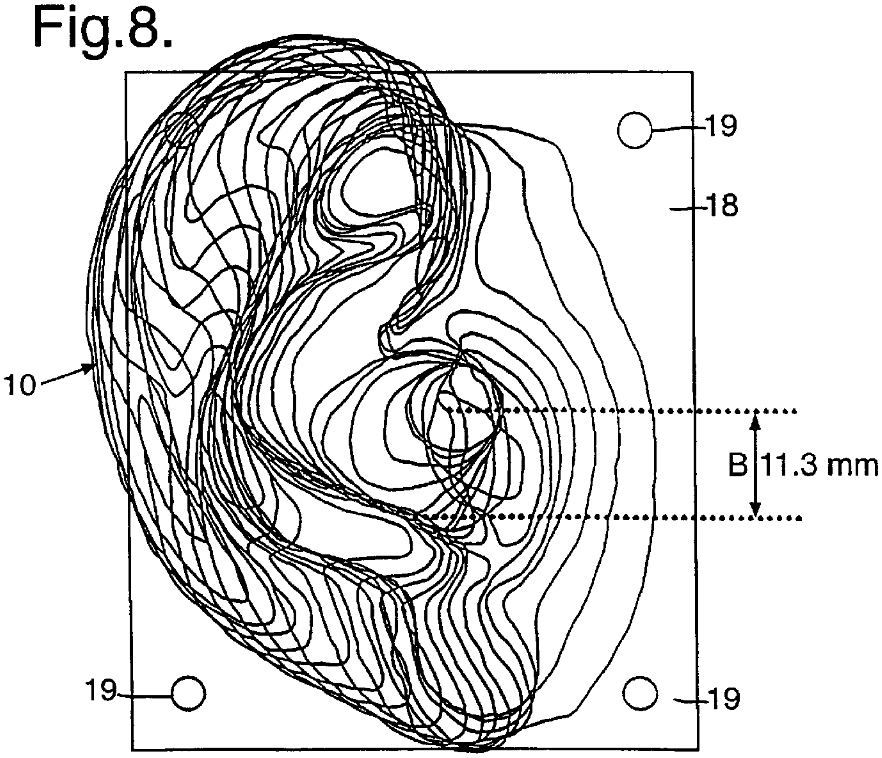

(c) The distance from the center of the canal entrance to concha floor (refer to FIG. 8) is critical. We have found that an average value should be 11.3 mm.

Figure 9:
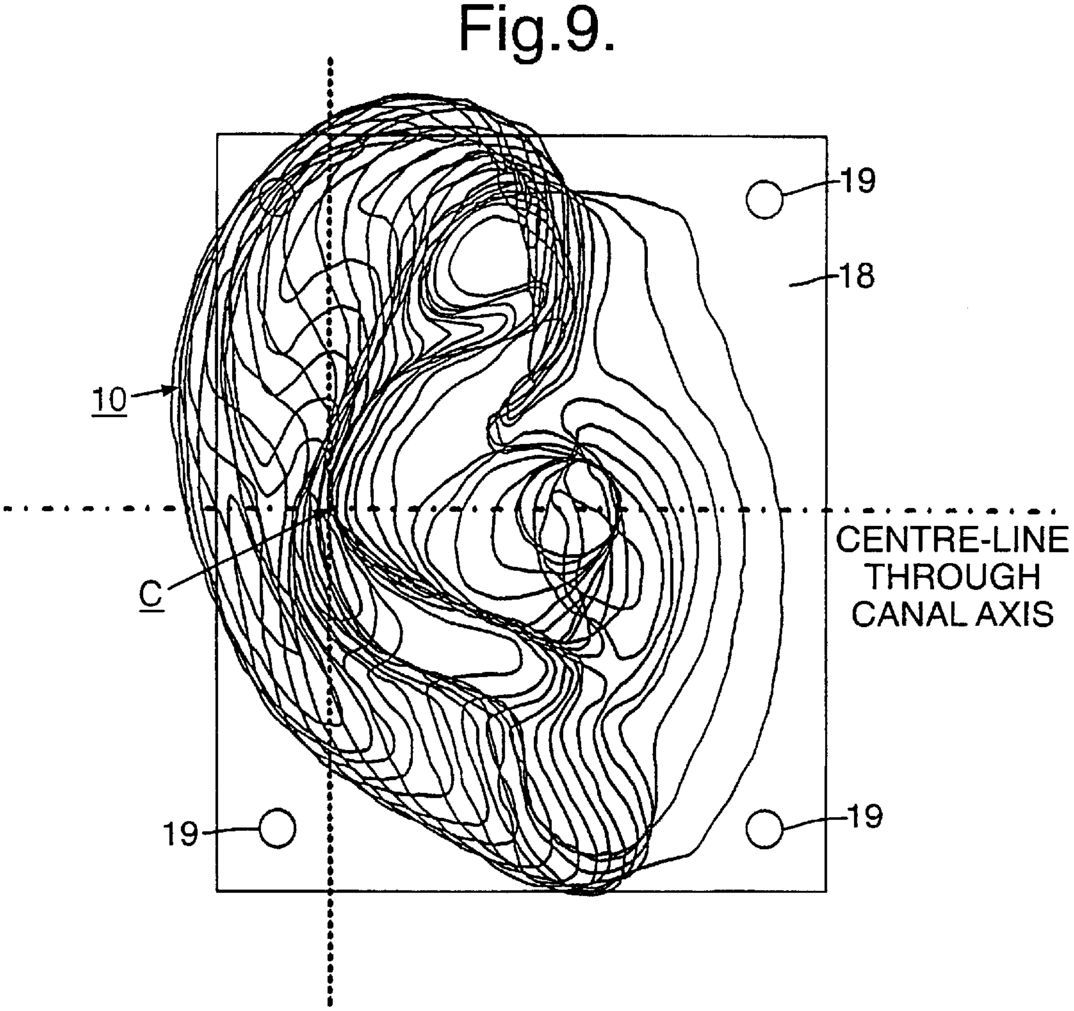

(d) The alignment of the point of inflection of the rear concha wall substantially horizontally with the center of the auditory canal entrance is very important, as is shown in FIG. 9.

Materials of construction were found not to be important (in contrast to claims in the U.S. Patent of Zuccarelli (U.S. Pat. No. 4,680,856). We have found no significant differences between very soft elastomers and hard, rigid plastics. It is the dimensions which are important, and it is preferred to use rigid plastics because they are easier to handle and they are dimensionally stable.

One might think that it is decidedly not the correct approach to build an artificial ear from a stack of 1 mm-thick laminates, (this thickness being a reasonable compromise between the final detail of the laminated structure and complexity of manufacture), because there might be acoustic interference problems caused by the discrete nature of the individual laminations, creating "stepped" edges. However, this is not the case, because the 1 mm quantum steps in the z-plane (stacking direction) correspond to very high frequencies—well above the range of normal hearing, which is typically 20 Hz to 20 kHz.

It is important to understand the role of the auditory canal in artificial head technology. The first prior known artificial heads did not incorporate artificial auditory canals, but merely inset the recording microphones into the pinnae with the microphone diaphragm elements positioned roughly where the auditory canal entrance would be situated. There are several reasons for this. Firstly, microphone diameters, especially those of studio quality, are much larger (20 mm and upwards) than the auditory canal diameter (7 or 8 mm), and so it would be physically difficult to mount such a microphone into a simulated auditory canal structure. Secondly the microphone would be set into a cavity, and therefore it would be less sensitive, and the cavity would be resonant, and therefore introduce unwanted comb-filtering effects.

In addition, in the past it was considered that the audio canal itself did not contribute to spatial effects, and that these were entirely due to the presence of the head and the shape of the pinnae. Almost without exception, when the presence of an artificial auditory canal has been considered important in the past, it was stated to be necessary purely for impedance-matching properties or for physical reasons, and NOT necessarily for the spatial properties of the system. In fact, there have been papers published which that the presence of an auditory canal is unnecessary for spatial properties. It is clear that one has to consider the design of the audio canal when one tests hearing-aid prostheses which intrude into the auditory canal, or ear-plugs ("ear defenders"), because one cannot use flush-mounted microphones. However in these circumstances the relevance of the performance on the spatial effects is not considered. One of the first reports of an artificial head assembly to feature auditory canal simulators is described in the 1966 paper of Bauer et al. (entitled External ear replica for acoustical testing, B B Bauer, A J Rosenheck and L A Abbagnaro, J. Acoust. Soc. Am., 1967, 42, (1), pp. 204–207) who based their auditory canal dimensions on the data of Olson ("Acoustical Engineering", Olson, (D Van Nostrand Co. Inc., Princeton, N.J., 1960), p. 559), namely 22 mm in length and 7.6 mm diameter. It seems certain that the length dimension was back-calculated from acoustic resonance measurements—it is unlikely actual physical measurements were made in view of the potential danger to the subjects. If this is true, then the measured 3.9 kHz resonance has been used to calculate an auditory canal length of 21.99 mm—but this assumes a right-angled termination to the auditory canal, which is incorrect, as will be described later. If one proceeds on this basis to make a 22 mm simulated auditory canal, with a 90° termination, then it will indeed feature the "correct" 3.9 kHz resonance, and one might believe that the simulation had been validated. However, our assertion below is that a 45° termination is needed for correct spatial response, and the length must be calculated differently in order to provide the correct, natural resonant frequency of 3.9 kHz.

The elemental resonant properties of the auditory canal are those of a tube closed at one end, and so the fundamental resonance occurs when one-quarter of a wavelength, $\lambda$, corresponds to the length of the tube, L, and hence $\lambda$=4L. Assuming the speed of sound in air to be 343 $ms^{-1}$, the resonant frequency, $f_r$ (kHz), can be calculated to be equal to 343/4L (where L is in mm). The auditory canal of Bauer and colleagues, referred to above, similar to that of Torick et al. described below), featured a published response characteristic which showed the fundamental resonance to exist at around 3.9 kHz, which is consistent with a length of 22 mm, according to this formula.

In the 1968 artificial head system of E L Torick et al. ; designed for the acoustical testing of personal communications devices, an auditory canal assembly was also incorporated. This was to ensure that the acoustical loading of the measurement system was representative of a real-life situation, and superior to the "6 cc" and "2 cc" acoustic couplers known at that time. Torick et al, attempted to match the acoustical constants of the auditory canal and tympanum by constructing a nearly cylindrical tube approximately 2.2 cm in length and 0.76 cm in diameter with a volume of 1 cc. Torick et al acknowledged that Zwislocki had reported an effective volume of approximately 1.6 cc for the combination of the ear auditory canal and eardrum, leading to the conclusion that the equivalent volume contribution by the eardrum (and possibly the compliance of the surround) is about 0.6 cc.

Torick and colleagues then proceeded to create a lumped-element transmission line model of the auditory canal, and mount a B&K 4132 microphone (with its grille present) axially into the end of a stepped tube, carrying a damping resistance in front of the microphone grille. The resistance was adjusted such that the overall impedance of the auditory canal/microphone system was similar to a real ear auditory canal. Although the authors were attempting to copy the geometry of the human arrangement, the microphone was mounted axially, (i.e. aligned with the auditory canal element). In reality, however, the tympanic membrane exists at an angle of around 45° facing downwards (and very slightly forwards).

However, when one considers the ear structure (see FIG. 1) more carefully, one can observe that it can be represented by two prime resonant elements: the concha cavity 12, and the auditory canal (not shown in FIG. 1). These are coupled together at right-angles (where the auditory canal entrance opens out into the innermost wall of the concha 12), and they constitute a serial pathway from the outside world to the tympanic membrane (not shown in FIG. 1). It seemed to us that the both of these resonant cavities, together with the manner of their coupling, must be critical elements which must be reproduced accurately if one is to construct a spatially accurate artificial head system. Not only must the pinna and auditory canal be reproduced correctly, but also the interface between the two is of equal, critical importance, especially in terms of its geometrical position.

Figure 10:
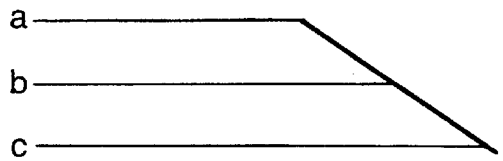
FIGS. 10 to 13 show schematically diagrams illustrating the calculation of suitable dimensions of an artificial auditory canal constructed in accordance with the present invention.

As has been referred to above, and is commonly stated in the literature, the human auditory canal resembles approximately a closed cylindrical tube of length 22 mm, and diameter of about 7 to 8 mm. This length corresponds to a fundamental (quarter-wave) resonant frequency of about 3.89 kHz for a 90° end termination. However, because the eardrum is actually disposed at an angle of 45° facing downwards, what exactly does the expression "auditory canal length" relate to? Referring to FIG. 10, which shows a cross section diagram of tube featuring 45° end termination, does it mean the center-line distance (b,), maximum length (c) or the minimum length (a)? One might reasonably expect the often-stated 22 mm auditory canal-length to be the center-line dimension, (b). However, if one constructs an artificial auditory canal with a 45° termination and a 22 mm center-line dimension, the resonant frequency—in practice—is measured to be about 3 kHz (in contrast to the requisite 3.9 kHz—a 23% difference). Why is this so?

The answer lies in the way in which wavefronts are reflected by the 45° end-termination, as follows.

Figure 11:
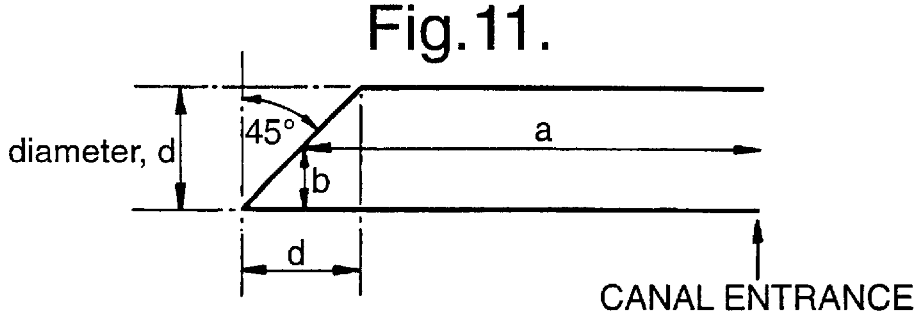

Consider a wavefront entering the auditory canal 23 along the center-line (FIG. 11). It progresses along its center-line length, (a) until it encounters the termination, at which point it undergoes a reflection sending the wavefront downwards, in this case, along path (b). When the wavefront encounters the auditory canal floor, it is reflected backwards exactly along its path, upwards to the termination, and thence outwards along the length and out of the entrance. Hence the effective length of the auditory canal, $L_{eff}$, is equal to the center-line distance (a), plus one-half of the auditory canal diameter (b): and therefore $L_{eff}$=(a+d/2).

Figure 12:
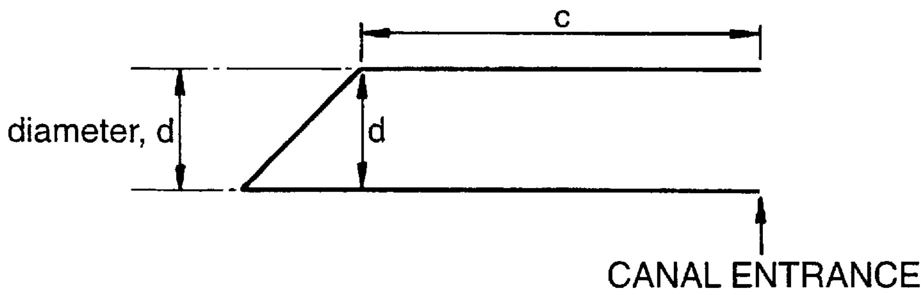

Consider now the wavefront entering and travelling along a path at the upper edge of the auditory canal 23 (FIG. 12). Because the termination is at 45°, the first path length, c. is equal to (a−d/2), and the second path length is equal to d, the diameter of the tube. Hence the effective path length in this case is equal to (a−d/2)+d. This is equal to (a+d/2), and is therefore exactly the same as in the previous case, where the wavefront path was central. By inspection, one can see also that, were the path to be along the lower edge of the auditory canal, then the effective path length would also be: $L_{eff}$=(a+d/2).

In summary: the effective resonant length of an open ended tube terminated by a 45° reflective boundary is equal to the sum of the length of the center-line between the entrance and the boundary, plus one half of the diameter of the tube. Using this method, one can now calculate the dimensions of a 45° auditory canal which features the required, physiological 3.9 kHz resonance. The effective length must be 22 mm, as before, so the center-line distance must be equal to 22 mm minus one-half of the diameter. If the tube is made to be 7 mm diameter, then the center-line distance is 18.5 mm. An auditory canal 23, therefore, which features the correct 45° angle of termination, and also possesses the correct physiological fundamental resonance of 3.9 kHz, has the dimensions shown in FIG. 13.

Figure 13:
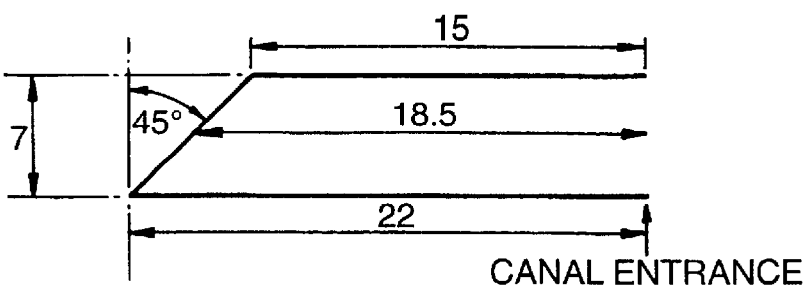

From FIG. 13 it is important to note that the upper section of the tube is quite short: (only two diameters in length). It is often stated in the literature that the auditory canal behaves as a one dimensional waveguide, because the wavelengths of sound in the audible spectrum are greater than the diameter of the auditory canal, and hence lateral propagation modes are not possible, only longitudinal propagation. Waveguiding phenomenon in other, confined structures is well known, for example in microwave conduits, optical fibers and integrated-optic devices. However, it can be shown that although mono-mode propagation conditions prevail in the waveguide at distances more than several wavelengths from the ends of the guide (the entrance and exit), they do not prevail near the ends. Consequently, it is wrong to dismiss the physical properties of the auditory canal as unimportant because the auditory canal "acts as a one-dimensional waveguide"; the eardrum (or microphone diaphragm) is sufficiently close to the entrance to disqualify this view. Hence, the termination of the auditory canal with a microphone mounted at 90°, as is known in the prior art, is not correct if valid and effective spatial attributes are required, such as for three-dimensional sound recording, or HRTF measurement.

One might think that there would be problems if non-flesh-like materials were used to make the auditory canal structure, but we have found that this is most certainly not true. In previous attempts to create artificial auditory canal assemblies, it is common to use metal or similar hard materials, although U.S. Pat. No. 4,680,856 (Zuccarelli) maintains that it is essential to copy the material properties of the human auditory canal Thus U.S. Pat. No. 4,680,856 explained > ". . . the first 8 mm of the auditory meatus (24 mm long) are preferably made of rubber, while the remaining 16 mm has an interior layer of plaster or the like to simulate respectively the fibro-cartilagenous and bony portions of the middle ear".

We have discovered that this claim is not important.

One might think that a very detailed copy of the auditory canal (or "auditory meatus") might be necessary for accurate spatial properties. Indeed, U.S. Pat. No. 4,680,856 (Zuccarelli) stated the following to be important.

> ". . . the system according to this invention have in the meatus a sharp dilation which acts like the muffler of an internal combustion engine", and:
>
> "Cavity . . . acting as the meatus has a section of an elliptical section cylinder with a torsion on its axis such that the wall in correspondence with the external orifice is anterior, inclining gradually so as to become lower front, while the posterior wall becomes upper rear. The flatter the former, the more highly convex is the latter".

In contrast to these complex descriptions, we have found that a simple metal (or plastic) auditory canal 23 featuring the above dimensional properties ((FIG. 13) provides excellent spatial properties, when used in conjunction with (and coupled correctly to) an effective pinna 10. In addition, the use of metal (or plastic) makes for easy manufacture, and provides effective acoustic isolation of the auditory canal in respect of conducted sound pick-up ("microphony") from the structure on which it is mounted.

One might think that there would be problems if an acoustically-reflective microphone were used, rather than a structure and material more like the tympanic membrane, but we have found this is not true either. In reality, the eardrum has a reflectivity of around 0.6, whereas the diaphragms and grids of most microphones will have a much greater value—probably around 0.95 or more. Consequently, the resonant properties of a microphone-terminated system feature a greater "Q" factor than would be representative of a human auditory canal, and so we have found it convenient to introduce a lightweight, open-pore foam-rubber damping plug 24 into the entire artificial auditory canal 23. This has the effect of reducing the magnitude of the resonant peak by about 5 dB, and it does not affect any other parts of the spectral response or the spatial properties of the assembly whatsoever.

Figure 14:
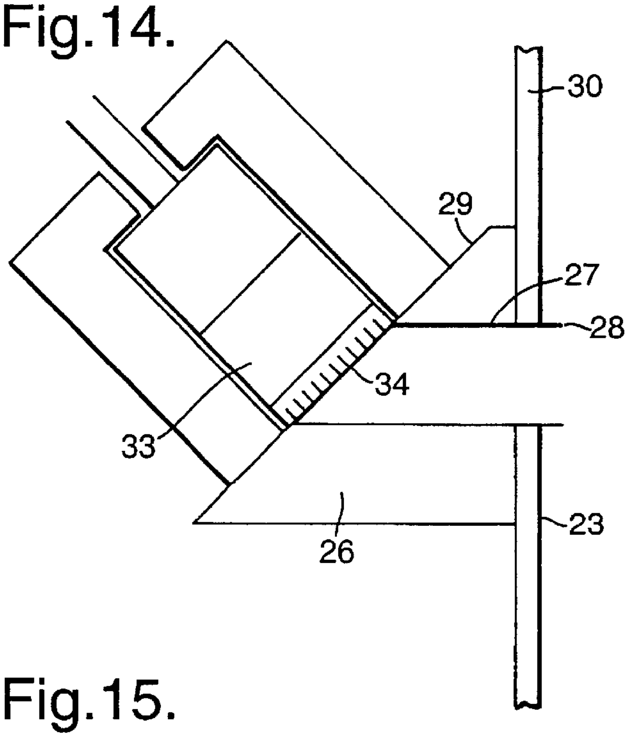
FIG. 14 shows schematically an artificial auditory canal and microphone assembly constructed in accordance with the present invention.
Figure 15:
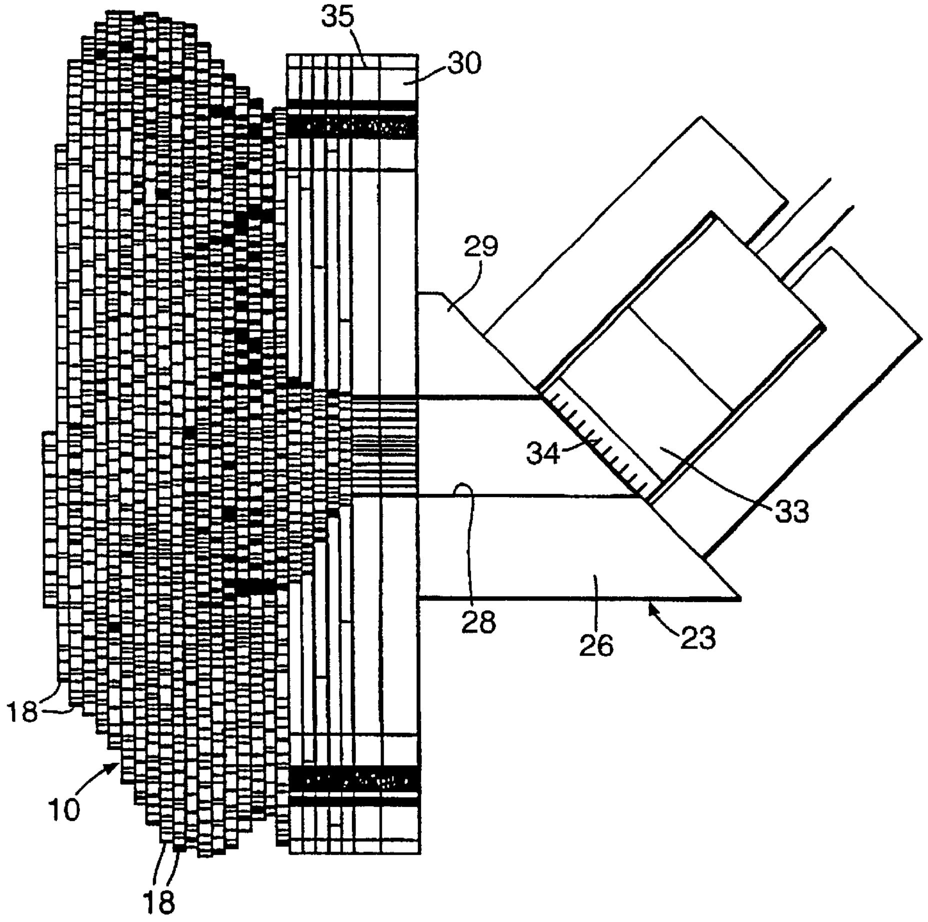
FIG. 15 shows schematically an end elevation of an artificial ear constructed in accordance with the present invention.

A section diagram showing a 12 mm studio-type microphone mounted on to an auditory canal assembly according to the present invention is shown in FIG. 14, and a complete ear/auditory-canal/microphone assembly is shown in FIG. 15 Referring to FIG. 14 the artificial auditory canal comprises a metal or plastic block 26 having a right circular cylindrical bore 27 of 8 mm diameter. A brass tube 28, having an inside diameter of 7 mm is fixed in the bore 27 of the block 26. The block 26 has a face 29 which is inclined at an angle of 45° to the longitudinal axis of the bore 27. Similarly one end of the tube 28 terminates in the same angled plane as face 29. The tube 28 extends through a 2 mm thick mounting plate 30 which enables the artificial auditory canal to be attached to the base of the artificial pinna 10. The tube 28 projects a distance of 3 mm from the plate 30.

A second block 31 having a central right circular cylindrical recess 32 of 12 mm diameter is fixed to the block 24 with the central axis of the recess 32 intersecting the longitudinal axis of the bore 27. A 12 mm diameter microphone 33 is mounted in the recess 32 with the grille 34 of the microphone lying in the plane of the confronting surfaces of the blocks 24 and 31.

Referring to FIG. 15 there is shown a side elevation of a laminated pinna 10, manufactured as described above, assembled as an integrated structure and fitted with an artificial auditory canal structure 23 constructed in accordance with FIG. 14. The artificial auditory canal 23 is attached to the artificial pinna 10 by means of the plate 30, is which both structures are bolted. The bolt holes in the pinna structure are shown (FIG. 6), but hose of the cancal have been omitted for clarity. A 2 mm thick spacer 35, is shown included here for experimental work; this can be glued to the base of the pinna 10.

The laminated pinnae manufactured according to the present invention may be used in an artificial-head recording system. In view of the fact that each laminated pinna is identical to a master set of images (the left and right pinna are built up by placing one set of supports 18 in reverse order in the jig) very precise recordings can be made because the sound waves received by each pinna are converted by the microphones in to electrical signals which can be processed (digitally) by a signal processor which uses algorithms and filters with head related transfer function derived from measurements corresponding exactly to the measurements of the actual laminated ears used to make the recordings. Clearly, identical matched pairs of laminated pinnae can be used in an artificial head recording system to generate the appropriate signal processing filters for use in other artificial head recording systems which may or may not be fitted with pinnae made by the present invention.

What is claimed is:

1. A method of manufacturing a laminated artificial pinna comprising the steps of:

(a) forming a three dimensional model of a human pinna in a first material, (b) encapsulating said model in a molding material, (c) machining away the encapsulated model to reveal a cross sectional shape of the model.

(d) making an image of the cross sectional shape revealed by step (c), (e) repeating step (c) incrementally to reveal cross sectional shapes of the model in spaced parallel planes and repeating step (d), (f) providing a plurality of blank self supporting sheets of material of a thickness corresponding to the distance between said spaced parallel planes, and using the image produced by step (d) to produce a replica of the cross sectional shape of the model pinna supported from each sheet of material by bridging supports.

(g) repeating step (f) for each cross-sectional shape revealed by step (c), and (h) assembling and gluing together a stack of said sheets to define a laminated replica of said model.

2. A method according to claim 1 wherein step (d) comprises the step of deriving from said image, data for controlling the direction of movement of a cutting tool, and step (f) comprises machining each sheet of material with a cutting tool programmed to move under control of the data derived by step (d).

3. A method according to claim 2 wherein the electronic image is used to derive a binary computer control code for controlling the direction of movement of a C.N.C. machine cutting tool.

4. A method according claim 1 wherein step (f) comprises the step of using the image produced by step (d) to produce a mask corresponding to said image, and step (f) comprises the step of removing unmasked material.

5. A method according to claim 4 wherein the sheets of material are photosensitive and the unmasked material is removed by exposing the masked sheets to light and a developer.

6. An artificial pinna according to claim 4 wherein the dimension of the sum of the length of the bore and the radius of the bore has within the range of (20 mm to 23 mm).

7. A method according to claim 1 wherein an artificial auditory canal is attached to the laminated replica of said model.

8. A method according to claim 1 wherein the model is made of a rigid plastics material.

9. A method according to claim 1 wherein the molding material is a rigid plastics material of a different color to that of the model.

10. A method according to claim 1 wherein the image is derived by electronically scanning a cross section of the encapsulated model.

11. A method according to claim 1 wherein the image is derived by photocopying a cross section of the encapsulated model.

12. A method according to claim 11 wherein the image is converted to a digitised electronic image.

13. An artificial pinna according to claim 11 wherein the diameter of the bore is 7 mm, the angle of the plane is 45° and the length is 18.5 m.

14. A laminated artificial pinna constructed in accordance with the method claimed in claim 1.

15. A laminated artificial pinna according to claim 14 characterized in that the artificial pinna has a concha, fossa and auditory canal, and the auditory canal is constructed and arranged relative to the concha, so that the distance from the center of the entrance of the auditory canal to the rear wall of the concha lies within the range of 15 mm to 20 mm, the distance from the center of the entrance of the auditory canal to the concha floor lies within the range of 9 mm to 15 mm, and the alignment canal to the concha floor lies within the range of 9 mm to 15 mm, and the alignment of the turning point with the center of the entrance of the auditory canal is substantially horizontal.

16. An artificial pinna according to claim 15 wherein the artificial auditory canal comprises a block having a bore extending through the block and terminating in a plane at an angle of 45° to the longitudinal axis of the bore and a microphone having a pressure sensitive face lying in said plane.

17. An artificial pinna according to claim 16 wherein the bore of the auditory canal comprises a right circular cylindrical bore having a radius and a length, measured from an open end of the bore along a central axis of the bore to the plane of the pressure sensitive face of the microphone which is such as to define a resonant cavity having a fundamental resonance of 3.9 KHz.

18. An ear according to claim 15 wherein the average distance (A) from the central axis of the bore of the auditory canal to the rear wall of the concha is 16.6 mm.

19. A pinna according to claim 15 wherein the average distance (B) from the canal axis to the floor of the concha is 11.3 mm.

20. A pinna according to claim 15 wherein the fossa has a volume of between 0.2 cc and 0.7 cc.

21. A pinna according to claim 20 wherein the average volume of the fossa is 0.5 cc.

22. An artificial head comprising a pair of laminated pinnae constructed in accordance with claim 1.

23. A method of recording sound using artificial ears having pinnae manufactured according to the method claimed in claim 1 wherein sound waves received by the artificial ears is converted to an electrical signal and is processed by a signal processor having signal filters, the head related transfer functions of which are derived from signal processing algorithms based on measurements corresponding to the measurements of the artificial pinna and auditory canals of the artificial ears which are used to make the recording.

* * * * *